(12) United States Patent
Friede et al.

(10) Patent No.: US 6,506,386 B1
(45) Date of Patent: Jan. 14, 2003

(54) VACCINE COMPRISING AN ISCOM CONSISTING OF STEROL AND SAPONIN WHICH IS FREE OF ADDITIONAL DETERGENT

(75) Inventors: Martin Friede, Farnham (GB); Nathalie Garcon, Wavre (BE)

(73) Assignee: SmithKline Beecham Biologicals, S.A., Rixensart (BE)

( * ) Notice: Subject to any disclaimer, the term of this patent is extended or adjusted under 35 U.S.C. 154(b) by 0 days.

(21) Appl. No.: 09/744,800

(22) PCT Filed: Aug. 3, 1999

(86) PCT No.: PCT/EP99/05587

§ 371 (c)(1),
(2), (4) Date: Jun. 4, 2001

(87) PCT Pub. No.: WO00/07621

PCT Pub. Date: Feb. 17, 2000

(30) Foreign Application Priority Data

Aug. 5, 1998 (GB) .............................................. 9817052

(51) Int. Cl.[7] .............................................. A61K 39/39
(52) U.S. Cl. ............................... 424/184.1; 424/278.1; 424/283.1; 514/25
(58) Field of Search ........................... 424/184.1, 278.1, 424/283.1, 208.1; 514/25

(56) References Cited

U.S. PATENT DOCUMENTS

| 5,620,690 A | 4/1997 | Kersten et al. |
| 5,679,354 A | 10/1997 | Morein et al. |
| 6,231,859 B1 * | 5/2001 | Kensil ..................... 424/184.1 |

FOREIGN PATENT DOCUMENTS

| WO | WO 96/11711 | 4/1996 |

OTHER PUBLICATIONS

Kersten, et al., "On the Structure of Immune–Stimulating Saponin–Lipid Complexes (Iscoms)", *Biochimica et Biophysica Acta*, 1062(2): 165–71 (1991).

Sjolander, et al., "Uptake and Adjuvant Activity of Orally Delivered Saponin and ISCOM™ Vaccines", *Advanced Drug Delivery Reviews*, 34: 321–338 (1998).

Barr, et al., "ISCOMs (Immunostimulating Complexes): The First Decade", *Immunology and Cell Biology*, 74: 8–25 (1996).

* cited by examiner

*Primary Examiner*—Laurie Scheiner
(74) *Attorney, Agent, or Firm*—Charles M. Kinzig; Edward R. Gimmi

(57) ABSTRACT

The present invention provides an improved adjuvant formulation and a process for producing said adjuvant. The adjuvant comprises an ISCOM structure comprising a saponin, said ISCOM structure being devoid of additional detergent.

15 Claims, 1 Drawing Sheet

Figure 1:
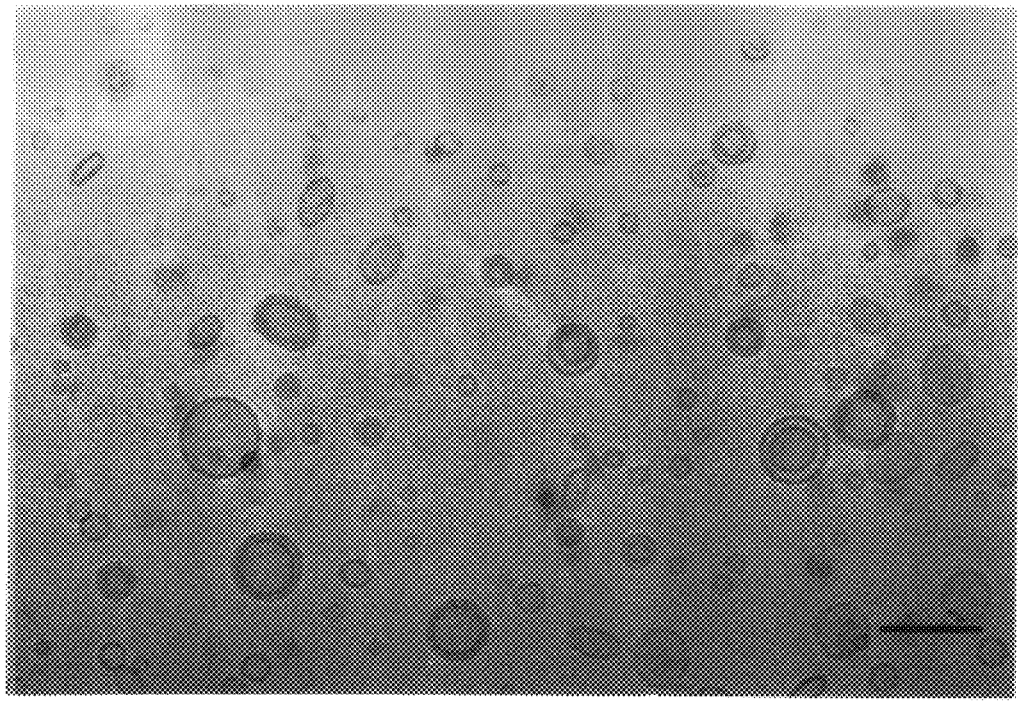

VACCINE COMPRISING AN ISCOM CONSISTING OF STEROL AND SAPONIN WHICH IS FREE OF ADDITIONAL DETERGENT

The present invention provides an improved adjuvant formulation and a process for producing said adjuvant. The adjuvant comprises an ISCOM structure comprising a saponin, said ISCOM structure being devoid of additional detergent. Also provided is an improved method of producing an adjuvant, and vaccines comprising the adjuvant of the present invention.

For many vaccines it is generally accepted that in order to generate significant levels of antigen specific immune responses, it is necessary to help the immune system by the inclusion of an adjuvant. The term adjuvant comes from the Latin of the verb "to Help" which is adjuvare. A number of adjuvants which help the immune response to a co-administered antigen to achieve greater magnitude than that observed if the antigen was given alone are known in the art. These include metallic salts, such as aluminium hydroxide or phosphate; liposomes, the bacterially derived monophosphoryl lipid A, Cholera toxin, and numerous others. Adjuvants may be classed as immunostimulants which have a direct stimulatory effect on the cells of the immune system, or may be classed as "vehicles" which function as carriers which present antigen to the immune system more efficiently than when the antigen is given alone. Alternatively, adjuvants may function in a combination of these mechanisms.

Specific adjuvants may also be used to drive the immune response into a particular desired characteristic. In theory, any given immune response may characterised into two mutually exclusive extremes of immune effector mechanisms. One extreme being predominantly a humoral response (characterised by the generation of Th2-type cytokines and immunoglobulin production) and a second extreme of a predominantly cell-mediated immune response (characterised by the generation of Th1-type cytokines and cytotoxic T cells). Generally speaking what is actually observed in real life is a balance of these two extremes, with any given response being described as being predominantly humoral (Th2-type) or predominantly cell-mediated (Th1-type). Thus for any particular pathogen, if it is desired that a vaccine should induce a predominantly Th1-type immune response, then the vaccine should be formulated with a known Th1-type inducing adjuvant.

One such adjuvant which is known to induce a balance of humoral and cell mediated immune response, which may include strong cell-mediated and also strong humoral responses, are the Immune-stimulating complexes (so called ISCOMs).

ISCOMs are three dimensional 'cage-like' structures which have been shown to form upon detergent removal from mixtures of saponins, detergents and cholesterol. ISCOMs and their use in vaccines are disclosed in EP 0 109 942 "Immunogenic protein or peptide complex, method of producing said complexes and use thereof as an immune stimulant and as a vaccine". This patent discloses ISCOMs comprising antigen with hydrophobic regions and a glycoside (saponin), characterised in that the complex has an open spherical structure consisting of circular subunits or parts of the spheric structure. ISCOMs are thus open structures of around 30 nm in diameter with a morphology which is different from liposomal structures. The ISCOMs and parts thereof also usually have a lower sedimentation constant than corresponding micelles and a higher sedimentation constant than the corresponding monomeric form of protein or peptide, and a higher sedimentation constant than the corresponding liposome. The classical "cage-like" structure of ISCOMs can be seen in the electron microscopy studies of EP 0 242 380 B1 and EP 0 180 564 B1.

During their manufacture, phospholipids or additional protein antigens may be included in the structure. These ISCOM-protein complexes have been used as very potent vaccines (EP 0 109 942 B1). Alternatively, preformed ISCOMs without any additional antigen may be mixed with extraneous antigen to form a vaccine wherein the antigen is not in a complex with the ISCOM (EP 0 436 620 B1). These vaccine formulations have also been shown to induce high levels of immune responses.

ISCOM/protein complexes have also been formed by the covalent conjugation of the protein antigen onto the surface of the ISCOM (EP 0 180 564 B1). The use of ISCOMs for mucosal vaccination has also been described Mowat et al. Immunology, 72, 317–322 (1991). The ISCOM structure has been improved for use in mucosal applications by the incorporation of membrane targeting proteins (WO 97/30728).

The saponins are plant derived glycosides, a number of which have been studied extensively for their biological properties (The Plant Glycosides, McIlroy, R. J., Edward Arnold and co., London, 1951). The saponins used most predominantly in the art for the production of ISCOMs are those derived from the plants Quillaja saponaria molina, *Aesculus hippocastanum* or *Gyophilla struthium*. Extracts of the bark of Quillaja saponaria molina which are known to have adjuvant activity are known in the art, for example Quil A (Dalsgaard, K., 1974, Saponin adjuvants III, Archiv.für dis Gesamte Virusforschung, 44, 243–254). Also pure fractions of Quil A have been described which retain adjuvant activity whilst being less toxic than Quil A, for example QS21 (EP 0 362 279 B1, and U.S. Pat. No. 5,057,540). QS21 is also described in Kensil et al. (1991. J. Immunology vol 146, 431–437).

ISCOMs comprising other purified less toxic fractions of Quil A have been used in the manufacture of vaccines. These structures have been reported to have adjuvant activity (WO 96/11711). Alternative particulate structures containing a saponin and a sterol, other than ISCOMs which are also less toxic than the saponin alone, have also been described (WO 96/33739).

Other saponins which have been described in the literature include Escin, which has been described in the Merck index ($12^{th}$ ed: entry 3737) as a mixture of saponins occuring in the seed of the horse chestnut tree, Lat: *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190). Fractions of escin have been purified and shown to be biologically active (Yoshikawa M, et al. (Chem Pharm Bull (Tokyo) 1996 August;44(8):1454–1464)). Sapoalbin from *Gypsophilla struthium* (R. Vochten et al., 1968, J. Pharm.Belg., 42, 213–226) has also been described in relation to ISCOM production.

ISCOMs are conventionally formed through two steps (e.g. as described in EP 0 109 942 ). 1, solubilisation of membrane and membrane proteins with detergent; 2, removal of solubilising agent by several means whilst at the same time contacting the membrane components with the saponin whose concentration is at least equal to the critical micellular concentration of the saponin, or removing the solubilising agent and directly transferring the antigen to the solution of saponin. U.S. Pat. No. Patent No. 4,578,269 teaches particular methods of separating the antigen from the solubilising agent. These methods include, amongst others: centrifugation through a gradient of solubilisation agent into an inverse gradient of saponin; or alternatively the solubilised antigen can be mixed with saponin followed by centrifugation of the mixture and dialysis to remove excess detergent.

EP 0 242 380 teaches of an improvement in this manufacturing process. This patent tells how the addition of lipids to the process prevents the formation of antigen/glycoside micelles, and ensures that the antigen/glycoside structures are all ISCOM-like. The specification states that the lipids may be added at any stage, at a molar ratio of at least 0.1:1 of lipids to antigen, and preferably 1:1. Examples of lipids include cholesterol and phosphatidyl choline. Thus, a method for producing an immunogenic complex between an antigen and a polar triterpensaponin, associated by the attraction between the hydrophobic regions of the triterpensaponin, lipid and antigen,
said complex must be formed by:
  (i) mixing antigen and lipid with a solubilising agent, thus forming complexes between the antigen, lipid and the solubilising agent, and
  (ii) removing the solubilising agent from the mixture in the presence of the saponin whose concentration is at least equal to the critical micellular concentration of the saponin, or removing the solubilising agent and directly transferring the mixture to the solution of saponin;
wherein the solubilisation agent is selected from a group comprising ionic or non-ionic detergents, Zwitterionic detergents, or detergents based on gallic acid;
wherein the complex has a higher sedimentation constant that the monomeric antigen,
and a lower sedimentation constant than the corresponding micelles;
and wherein the complex has an open spherical structure,
the improvement comprising adding to the solubilised antigen at least one lipid selected from the group comprising of fats, glycerol ethers, waxes, phospholipids, glycolipids, isoprenoids, steroids, and mixtures thereof, prior to the contact of the solubilised antigen with the glycoside-containing solution. Alternatively, ISCOMs have been produced using the solubilising agent to solubilise the antigen and/or lipids, followed by the spontaneous formation of the ISCOM structure without the removal of the solubilising agent. U.S. Pat. No. 4,981,684, EP 0 415 794 A1, and EP 0 766 967 A1 all teach a process for the production of ISCOMs with water insoluble antigens. This process comprises the solubilising of the antigen in a solubilising agent, admixing the solubilised antigen, a glycoside and a sterol and forming ISCOMs without the removal of the solubilising agent.

ISCOMs produced without antigen, so called Iscomatrix, have also been described WO 96/11711.

Thus, several process for the manufacture of ISCOMs have been described. All of these processes require the presence of an additional detergent other than the saponin itself. The ISCOMs are then either removed from the vaccine by dialysis or centrifugation, or are left in the vaccine formulation.

Despite the attempt at detergent removal in some of these methods, all of the resultant ISCOMs adjuvants or vaccines will contain some additional detergent, other than the saponin itself. Detergents by their very nature associate with lipid membranes, and so will never be totally removed. Furthermore, the dialysis method of removing substances works on a principle of equilibrium, thus, it is physically impossible to remove all traces of the detergent. Such formulations containing residual detergent may be less stable and more toxic than the adjuvants of the present invention without the detergent being present.

Examples of detergents that have been used in the production of ISCOMs include, sodium cholate, n-Octyl glucopyranoside, polyoxyethylene ethers or phenyl ethers, TritonX-100 (octylphenolether of polyethylene oxide), acylpolyoxyethylene esters, acyl polyoxyethylene sorbitan esters (the Tween series), the SPAN series, ionic detergents such as the gallic acid detergents (bile salts).

The present invention provides for adjuvant formulations comprising a saponin and a sterol, characterised in that the adjuvant is in the form of an ISCOM, and that said ISCOM is free of additional detergent, other than the saponin.

Also, provided is a process for the production of an ISCOM comprising a saponin and a sterol, characterised in that the process is free of additional detergents, other than the saponin.

Vaccines are also provided by the present invention comprising an adjuvant formulation comprising a saponin and a sterol, characterised in that the adjuvant is in the form of an ISCOM, and that said ISCOM is free of additional detergent, other than the saponin, and an antigen.

Preferably, the process of the present invention comprises two steps:
  1. The formation of cholesterol containing small unilamellar liposomes (SUL) in the absence of detergent, and;
  2. Admixing the preformed liposomes with saponin at a ratio of saponin:cholesterol (w/w) exceeding 1.

Adjuvant formulations thus formed are in the form of an ISCOM, said ISCOMs being free of detergent.

Optionally the SUL may be formed in the presence of antigen such that SUL are formed in association with antigen. This may be particularly preferable when using hydrophobic antigen. Also, the SUL may be formed in the presence of reactive phospholipids such as phosphatidyl ethanolamine or phosphatidyl serine or chemically derivatised forms thereof such that antigen may be conjugated to the ISCOM using commonly known heterobifunctional cross-linkers, such as SPDP. Alternatively a vaccine may be formed by simple admixing of the ISCOMs formed by the process of the present invention, or ISCOMs which are free of additional detergent, with antigen.

In order for a vaccine or adjuvant to be suitable for administration into a human, it has to comply with rigorous safety and quality control checks. Currently, there is no detergent available which is generally recognised as safe for injection. All detergents used to date in the production of ISCOMs are liable to be reactogenic, and induce cell lysis and necrosis at the site of injection. Thus, any ISCOM based vaccines containing even trace amounts of detergents must be supported by extensive reactogenicity and safety studies before gaining regulatory approval.

The adjuvants and vaccines of the present invention do not by definition have this requirement as they do not contain any detergent. The reactogenicity studies required for such vaccines and adjuvants only have to focus on the role of the saponin. It is, therefore, much easier to gain approval for these "clean" ISCOM products, than it is for vaccines containing additional reactogenic material.

A vaccine manufacturer must produce large quantities of a product in a manner which is reproducible and susceptible to quality control (QC) and Good Manufacturing Processing conditions (GMP). The methods previously used for the removal of detergent from ISCOMs are difficult to control under these conditions. For example, the scaling up of dialysis process is limited by the size of the dialysis equipment, and is also inherently variable depending on many factors including ambient temperature and media osmolarity. Equally, the scale of ISCOM production using the centrifuge method was previously dependent of the size of your centrifuge. Thus, it is difficult to produce a product using the previous methods in a large scale, controlled and reproducible manner. The process of the present invention is not limited by the size of any equipment, it is also susceptible to QC and GMP control throughout the process. For example a batch of liposomes may be produced and released for sterility and size, also a batch of saponin may be released for sterility and purity, all before the liposomes and saponin are admixed.

The presence or absence of additional detergent in the final preparations of ISCOMs formed by the classical methods can be determined by gas chromatography, or HPLC.

The process of the present invention does not require this variable detergent removal step and is therefore much easier to control. Each intermediate used in the process of the present invention may be produced and released from a QC point of view before the final step of admixing the preformed liposomes with the saponin. Additionally, the process of the present invention is not limited in the quantity of the final product.

The adjuvants of the present invention are suitable for administration to the recipient via any route, including systemic routes such as intramuscular or subcutaneous or transdermal, or via a mucosal route such as intranasal or oral. Saponin based adjuvant formulations which are not haemolytic are known (WO 96/33739). However, in certain circumstances the adjuvant of the present invention may beneficially retain significant haemolytic activity of the saponin, for example when used as an intranasal vaccine, or when some reactogenicity may be tolerated.

The SUL formed during the process of the present invention may be manufactured using well known techniques of the art. Such processes which do not involve additional detergent include sonication, microfluidisation, or membrane extrusion. For example phosphatidyl choline (PC) dissolved in ethanol may be added to a flask and dried under vacuum or inert gas. PBS or other pharmaceutically acceptable excipient may then be added and the contents of the flask sonicated. Optionally the lipid suspension may be microfluidised to attain a uniform preparation of SUL of around 100 nm in diameter. The SUL comprise cholesterol and also include one or more phospholipids. The ratio of cholesterol to phospholipid is at most 50% and preferably 20–25% (w/w). The phospholipid is preferably phosphatidylcholine and is most preferably chosen so as to have a low transition temperature e.g. Dioloeoylphosphatidylcholine or dilauryl phosphatidylcholine. Optionally a charged phospholipid (e.g. phosphatidylglycerol or phosphatidyl serine) may be added.

The saponins for use in the present invention include saponins derived from Quillaja Saponaria Molina, *Aesculus hippocastanum* or *Gyophilla struthium*. Particularly preferred saponins are QuilA or extracts therefrom from Quillaja Saponaria Molina. Particularly preferred extracts from Quil A include QS21. Typically for human administration the saponin will be present in a vaccine in the range 1 $\mu$g–100 $\mu$g, preferably 10 $\mu$g–50 $\mu$g per dose.

The adjuvants of the present invention comprise a sterol. Ratios of saponin:sterol in adjuvants of the present invention is substantially in the range between 1:1 to 100:1 (w/w), preferably between 1:1 to 10:1 (w/w), and most preferably 5:1 (w/w). The sterol is preferably cholesterol.

Preferably the vaccine formulations of the present invention contain an antigen or antigenic composition capable of eliciting an immune response against a human pathogen, which antigen or antigenic composition is derived from HIV-1, (such as tat, nef, gp120 or gp160), human herpes viruses, such as gD or derivatives thereof or Immediate Early protein such as ICP27 from HSV1 or HSV2, cytomegalovirus ((esp Human)(such as gB or derivatives thereof), Rotavirus (including live-attenuated viruses), Epstein Barr virus (such as gp350 or derivatives thereof), Varicella Zoster Virus (such as gpI, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, . . . ), flaviviruses (e.g. Yellow Fever Virus, Dengue Virus, Tick-borne encephalitis virus, Japanese Encephalitis Virus) or Influenza virus, or derived from bacterial pathogens such as Neisseria spp, including *N. gonorrhea* and *N. meningitidis* (for example capsular polysaccharides and conjugates thereof, transferrin-binding proteins, lactoferrin binding proteins, PilC, adhesins); Streptococcus spp, including *S. pneumoniae* (for example capsular polysaccharides and conjugates thereof, PsaA, PspA, streptolysin, choline-binding proteins), *S. pyogenes* (for example M proteins or fragments thereof, C5A protease, lipoteichoic acids), *S. agalactiae, S. mutans*; Haemophilus spp, including *H. influenzae* type B (for example PRP and conjugates thereof), non typeable *H. influenzae* (for example OMP26, high molecular weight adhesins, P5, P6, lipoprotein D), *H. ducreyi*; Moraxella spp, including *M catarrhalis*, also known as *Branhamella catarrhalis* (for example high and low molecular weight adhesins and invasins); Bordetella spp, including *B. pertussis* (for example pertactin, pertussis toxin or derivatives thereof, filamenteous hemagglutinin, adenylate cyclase, fimbriae), *B. parapertussis* and *B. bronchiseptica*; Mycobacterium spp., including M. tuberculosis (for example ESAT6, Antigen 85A, -B or -C), *M. bovis, M. leprae, M. avium, M. paratuberculosis, M. smegmatis*; Legionella spp, including *L. pneumophila*; Escherichia spp, including enterotoxic *E. coli* (for example colonization factors, heat-labile toxin or derivatives thereof, heat-stable toxin or derivatives thereof), enterohemorragic *E. coli* enteropathogenic *E. coli* (for example shiga toxin-like toxin or derivatives thereof); Vibrio spp, including *V. cholera* (for example cholera toxin or derivatives thereof); Shigella spp, including *S. sonnei, S. dysenteriae, S. flexnerii*; Yersinia spp, including *Y* enterocolitica (for example a Yop protein), *Y. pestis, Y. pseudotuberculosis*; Campylobacter spp, including *C. jejuni* (for example toxins, adhesins and invasins) and *C. coli*; Salmonella spp, including *S. typhi, S. paratyphi, S. choleraesuis, S. enteritidis*; Listeria spp., including *L. monocytogenes*; Helicobacter spp, including *H. pylori* (for example urease, catalase, vacuolating toxin); Pseudomonas spp, including *P. aeruginosa*, Staphylococcus spp., including *S. aureus, S. epidermidis*; Enterococcus spp., including *E. faecalis, E. faecium*; Clostridium spp., including *C. tetani* (for example tetanus toxin and derivative thereof), *C. botulinum* (for example botulinum toxin and derivative thereof), *C. difficile* (for example clostridium toxins A or B and derivatives thereof); Bacillus spp., including *B. anthracis* (for example botulinum toxin and derivatives thereof);

Corynebacterium spp., including *C. diphtheriae* (for example diphtheria toxin and derivatives thereof); Borrelia spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii*; Ehrlichia spp., including *E. equi* and the agent of the Human Granulocytic Ehrlichiosis; Rickettsia spp, including *R. rickettsii*; Chlamydia spp., including *C. trachomatis* (for example MOMP, heparin-binding proteins), *C. pneumoniae* (for example MOMP, heparin-binding proteins), *C. psittaci*; Leptospira spp., including *L. interrogans*; Treponema spp., including *T. pallidum* (for example the rare outer membrane proteins), *T. denticola, T. hyodysenteriae*; or derived from parasites such as Plasmodium spp., including *P. falciparum*; Toxoplasma spp., including *T. gondii* (or example SAG2, SAG3, Tg34); Entamoeba spp., including *E. histolytica*; Babesia spp., including *B. microti*; Trypanosoma spp., including *T. cruzi*; Giardia spp., including *G. lamblia*; Leshmania spp., including *L. major*; Pneumocystis spp., including *P. carinii*; Trichomonas spp., including *T. vaginalis*; Schisostoma spp., including *S. mansoni*, or derived from yeast such as Candida spp., including *C. albicans*; Cryptococcus spp., including *C. neoformans*.

Derivatives of Hepatitis B Surface antigen are well known in the art and include, inter alia, those PreS1, PreS2 S antigens set forth described in European Patent applications EP-A-414 374; EP-A-0304 578, and EP 198-474. In one preferred aspect the vaccine formulation of the invention comprises the HIV-1 antigen, gp120, especially when expressed in CHO cells. In a further embodiment, the vaccine formulation of the invention comprises gD2t as hereinabove defined.

In a preferred embodiment of the present invention vaccines containing the claimed adjuvant comprise the HPV viruses considered to be responsible for genital warts, (HPV 6 or HPV 11 and others), and the HPV viruses responsible for cervical cancer (HPV16, HPV18 and others). Particularly preferred forms of vaccine comprise L1 particles or capsomers, and fusion proteins comprising one or more antigens selected from the HPV 6 and HPV 11 proteins E6, E7, L1, and L2. The most preferred forms of fusion protein are: L2E7 as disclosed in GB 95 15478.7, and proteinD(1/3)-E7 disclosed in GB 9717953.5.

Vaccines of the present invention further comprise antigens derived from parasites that cause Malaria. For example, preferred antigens from *Plasmodia falciparum* include RTS,S and TRAP. RTS is a hybrid protein comprising substantially all the C-terminal portion of the circumsporozoite (CS) protein of *P.falciparum* linked via four amino acids of the preS2 portion of Hepatitis B surface antigen to the surface (S) antigen of hepatitis B virus. It's full structure is disclosed in the International Patent Application No. PCT/EP92/02591, published under Number WO 93/10152 claiming priority from UK patent application No.9124390.7. When expressed in yeast RTS is produced as a lipoprotein particle, and when it is co-expressed with the S antigen from HBV it produces a mixed particle known as RTS,S. TRAP antigens are described in the International Patent Application No. PCT/GB89/00895, published under WO 90/01496. A preferred embodiment of the present invention is a Malaria vaccine wherein the antigenic preparation comprises a combination of the RTS,S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27/25, Pfs16, Pfs48/45, Pfs230 and their analogues in Plasmodium spp.

The formulations may also contain an anti-tumour antigen and be useful for the immunotherapeutic treatment cancers. For example, the adjuvant formulation finds utility with tumour rejection antigens such as those for prostrate, breast, colorectal, lung, pancreatic, renal or melanoma cancers. Exemplary antigens include MAGE 1 and MAGE 3 or other MAGE antigens for the treatment of melanoma, PRAME, BAGE or GAGE (Robbins and Kawakami, 1996, Current Opinions in Immunology 8, pps 628–636; Van den Eynde et al., International Journal of Clinical & Laboratory Research (submitted 1997); Correale et al. (1997), Journal of the National Cancer Institute 89, p293. Indeed these antigens are expressed in a wide range of tumour types such as melanoma, lung carcinoma, sarcoma and bladder carcinoma. Other Tumor-Specific antigens are suitable for use with adjuvant of the present invention and include, but are not restricted to Prostate specific antigen (PSA) or Her-2/neu, KSA (GA377), MUC-1 and carcinoembryonic antigen (CEA). Accordingly in one aspect of the present invention there is provided a vaccine comprising an adjuvant composition according to the invention and a tumour rejection antigen.

It is foreseen that compositions of the present invention will be used to formulate vaccines containing antigens derived from Borrelia sp. For example, antigens may include nucleic acid, pathogen derived antigen or antigenic preparations, recombinantly produced protein or peptides, and chimeric fusion proteins. In particular the antigen is OspA. The OspA may be a full mature protein in a lipidated form virtue of the host cell (*E.Coli*) termed (Lipo-OspA) or a non-lipidated derivative. Such non-lipidated derivatives include the non-lipidated NS1-OspA fusion protein which has the first 81 N-terminal amino acids of the non-structural protein (NS1) of the influenza virus, and the complete OspA protein, and another, MDP-OspA is a non-lipidated form of OspA carrying 3 additional N-terminal amino acids.

Vaccines of the present invention may be used for the prophylaxis or therapy of allergy. Such vaccines would comprise allergen specific (for example Der p1) and allergen non-specific antigens (for example the stanworth decapeptide).

Preferably, antigens to be used in the present invention are provided in aqueous solution or aggregates in aqueous suspension. Also forming part of the present invention are antigens with are present in a detergent containing solution or suspension. Thus vaccines of this type comprise ISCOM structure which are free of detergent, in the presence of external antigen in a solution or suspension of detergent.

The amount of protein in each vaccine dose is selected as an amount which induces an immunoprotective response without significant, adverse side effects in typical vaccinees. Such amount will vary depending upon which specific immunogen is employed and how it is presented. Generally, it is expected that each dose will comprise 1–1000 $\mu$g of protein, preferably 1–500 $\mu$g, preferably 1–100 $\mu$g, most preferably 1 to 50 $\mu$g. An optimal amount for a particular vaccine can be ascertained by standard studies involving observation of appropriate immune responses in subjects. Following an initial vaccination, subjects may receive one or several booster immunisation adequately spaced.

Also provided by the present invention is a process for the manufacture of an vaccine composition comprising the following steps: (1) the formation of cholesterol containing small unilamellar liposomes (SUL) in the absence of detergent; (2) admixing the preformed liposomes with saponin at a ratio of saponin:cholesterol (w/w) exceeding 1; (3) admixing an antigen with the product of step 2.

The formulations of the present invention maybe used for both prophylactic and therapeutic purposes. Accordingly, the present invention provides for a method of treating a mammal susceptible to or suffering from an infectious disease or cancer, or allergy, or autoimmune disease. In a further aspect of the present invention there is provided a vaccine as herein described for use in medicine. Furthermore, use of an vaccine in the manufacture of a medicament for the immunoprophylaxis or therapy of disease or infection or cancer is also provided. Vaccine preparation is generally described in New Trends and Developments in Vaccines, edited by Voller et al., University Park Press, Baltimore, Md., U.S.A. 1978.

The present invention is illustrated but not restricted by the following examples.

EXAMPLE 1

Preparation of ISCOMS by Addition of QS21 to Small Unilamellar Liposomes (SUL).

Dioloeoyl phosphatidylcholine (1 g) in ethanol was mixed with cholesterol (250 mg) in ethanol (solubilised by warming) and the ethanol removed under vacuum. Phosphate buffered saline (25 ml) was added and the flask agitated to suspend the lipids. The resulting multilamellar liposomes were microfluidised until the particle size was 100 nm as determined by photon correlation spectroscopy. The liposomes were filter sterilised through 0.22 µm filters and stored at 4° C.

QS21 (obtained from Aquila Biopharmaceuticals, Mass.) was dissolved in water at 2 mg/ml, the pH adjusted to 7 with HCl, and the solution filter sterilised through sterile 0.22 µm filters. To 100 µl of this solution (200 µg QS21) was added 20 µl SUL (containing 40 µg cholesterol).

Figure 2:
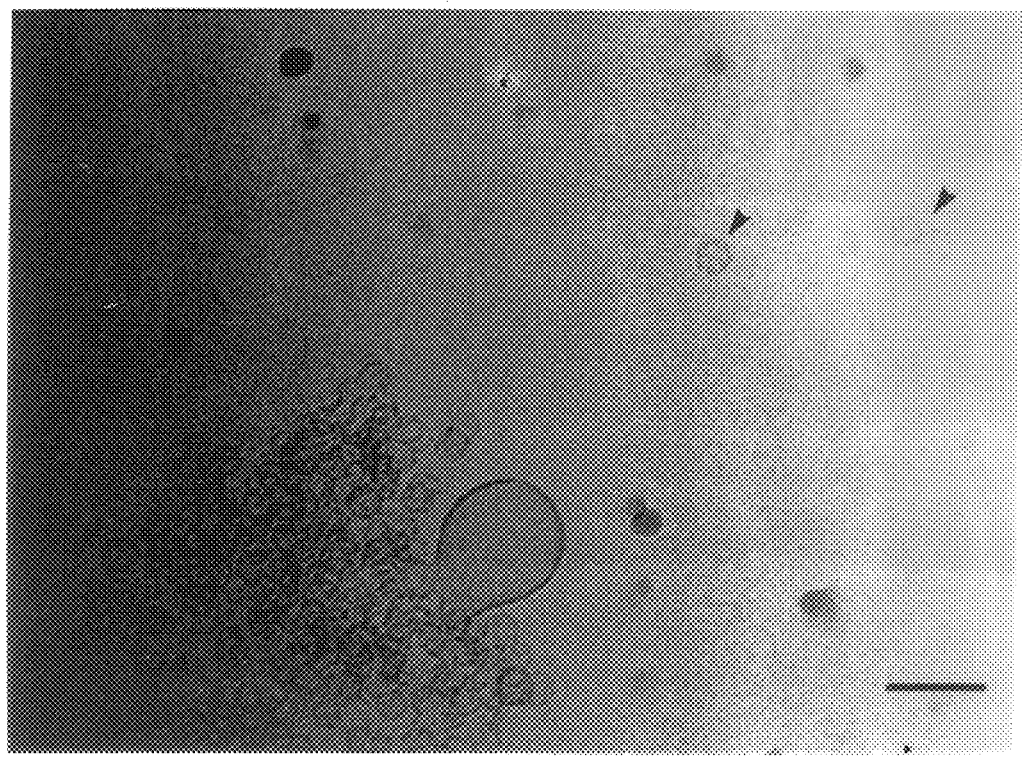

The original SUL and the QS21-SUL mixture were examined by transmission electron microscopy of frozen hydrated material (cryo-electron microscopy). FIG. 1 shows that the SUL are predominantly spherical unilamelar vesicles with size ranging from 40 to 200 nm. FIG. 2 shows that when the QS21 is added at a five-fold excess over cholesterol the vesicular structures disappear and are replaced by spherical cage-like structures. These closely resemble the open spherical ISCOM structure. In FIG. 2 there is also evidence of ISCOMs in the process of being formed by budding off from a vesicle. In the micrographs the bar represents 100 nm. Arrow heads point towards clearly discernible open spherical structures resembling ISCOMs.

EXAMPLE 2

Comparison of Density of SUL and ISCOMs Prepared by Adding QS21 to SUL.

SUL were prepared as in example 1 except that a trace of radioactive ($^3$H) cholesterol was included and the SUL were prepared by sonication. ISCOMs were prepared by adding QS21 directly to these SUL at a QS21:cholesterol ratio of 5:1.

The samples were layered onto a 10–60% sucrose gradient and centrifuged in an SW-40 rotor 34000 rpm and fractions collected and analysed for radioactivity. The radioactivity associated with the SUL was found only at the top of the gradient, whereas most of the radioactivity associated with the ISCOMs formed by adding QS21 to the SUL was found further down the tube indicating the ISCOMs have a higher density than the liposomes.

What is claimed is:

1. An adjuvant composition comprising a sterol, a saponin, and a phospholipid, characterised in that the adjuvant is in the form of an ISCOM and that it is free of additional detergent, other than the saponin.

2. An adjuvant composition as claimed in claim 1, wherein the ratio of saponin:sterol (w/w) exceeds 1.

3. An adjuvant composition as claimed in claim 1, wherein the ratio of saponin to sterol is in the range of 1:1 to 100:1 (w/w).

4. An adjuvant composition as claimed in claim 1, wherein the ratio of saponin to sterol is 5:1.

5. An adjuvant composition as claimed in any one of claims 1 to 4, wherein the saponin is Quil A or extract thereof.

6. An adjuvant composition as claimed in claim 5, wherein the extract of Quil A is QS21.

7. An-adjuvant composition as claimed in claim 1, wherein the sterol is cholesterol.

8. An adjuvant composition as claimed in claim 1, wherein the phospholipid is phosphatidylcholine.

9. An adjuvant composition as claimed in claim 8, wherein phosphatidylcholine is dioloeoylphosphatidylcholine or dilauryl phosphatidylcholine.

10. An adjuvant composition as claimed in claim 7, wherein the ratio of cholesterol to phospholipid is 50% (w/w).

11. An adjuvant composition as claimed in claim 10, wherein the ratio of cholesterol to phospholipid is 20–25% (w/w).

12. A vaccine comprising an adjuvant composition as claimed in any one of claims 1 to 11, further comprising an antigen.

13. A vaccine composition as claimed in claim 12, wherein the antigen is an antigen or antigenic composition derived from any of Human Immunodeficiency Virus, Feline Immunodeficiency Virus, Varicella Zoster virus, Herpes Simplex Virus type 1, Herpes Simplex virus type 2, Human cytomegalovirus, Hepatitis A, B, C, or E, Respiratory Syncytial virus, human papilloma virus, Influenza virus, Hib, Meningitis virus, Salmonella, Neisseria, Borrelia, Chlamydia, Bordetella, Plasmodium, or Toxoplasma.

14. A process for the manufacture of an adjuvant composition, comprising the following steps:

(a) the formation of cholesterol containing small unilamellar liposomes (SUL) in the absence of detergent; and (b) admixing the preformed liposomes with saponin at a ratio of saponin:cholesterol (w/w) exceeding 1.

15. A process for the manufacture of a vaccine composition, comprising the following steps:

(a) taking an adjuvant composition produced according to the process of claim 14; and (b) adding an antigen or an antigenic composition.

* * * * *